US005759543A

United States Patent [19]

Morozova et al.

[11] Patent Number: 5,759,543

[45] Date of Patent: Jun. 2, 1998

[54] APPLICATION OF A CELL CULTURE OF A FUSARIUM FUNGUS STRAIN PRODUCER FOR MEDICAL USES

[75] Inventors: Galina Rostislavovna Morozova; Alexandr Lvovich Morozov, both of Moscow, Russian Federation

[73] Assignee: Krestyanskoe Khozyaistvo "AGROFIRMADIZHA", Miakop, Russian Federation

[21] Appl. No.: 507,376

[22] PCT Filed: Nov. 23, 1994

[86] PCT No.: PCT/RU94/00260

§ 371 Date: Aug. 21, 1995

§ 102(e) Date: Aug. 21, 1995

[87] PCT Pub. No.: WO95/17902

PCT Pub. Date: Jul. 6, 1995

[30] Foreign Application Priority Data

Dec. 21, 1993 [RU] Russian Federation ............ 93057876

[51] Int. Cl.$^6$ ............................ A61K 35/72; C12N 1/14

[52] U.S. Cl. ....................................... 424/123; 435/254.7

[58] Field of Search ................................ 424/93.5, 123; 435/252.1, 254.1, 254.7, 260, 261

[56] References Cited

FOREIGN PATENT DOCUMENTS 2 384 501 10/1978 France .

*Primary Examiner*—Jean C. Witz
*Assistant Examiner*—Susan Hanley
*Attorney, Agent, or Firm*—Wigman, Cohen, Leitner & Myers, P.C.

[57] ABSTRACT

The invention describes utilization of a cell culture of the strain of fungus *Fusarium sambucinum* Fuckel var. *ossicolum* (Berk. et Curt.) Bulai VSB-917 (All-Union Collection of Industrial Microorganisms of the VNIIgenetika Institute, collection code VKPM F-168) for application in the capacity of a producer of physiologically active substances for prophylactic and curative purposes.

15 Claims, No Drawings

APPLICATION OF A CELL CULTURE OF A FUSARIUM FUNGUS STRAIN PRODUCER FOR MEDICAL USES

FIELD OF ART

The present invention relates to mycology and medicine and, more particularly, to the strains of fungi-producers of physiologically-active substances and preparations on their base for use in public health services.

BACKGROUND OF THE INVENTION

The strain of a higher fungus INONOTUS OBLIQUUS and the befungin preparation developed on its base are well known to those skill in the art.

Befungin is an extract from the excrescences growing on birch trees under the effect of this fungus. The preparation is a semi-fluid mass containing 30% of dry matter with 1% of cobaltichloride or 1.5% of cobaltisulfate added. It is used as a symptomatic medicine improving the state of health of patients suffering from chronic gastritis and dyskinesia of gastroenteric tract with prevailing atonia (M. D. Mashkovsky, Medicinal Agents, "Meditsina" publishers, Moscow, 1984, Vol. 2, p. 162).

However, the resources of untreated birch fungus for manufacture of befungin are extremely low, same as is the spectrophysiological effect of the preparation.

It is also known that the fungi *Lentinus edodes, Ganoderma lucidum, Pleurotis ostreatus* produce and antischlerotic effect and influence the content of cholesterin, normalizing its level in the organism (Lee Khva Rei, Vasiliyev L. V., Orekhov L. N., Tertov V. V., Tutyan V. A. "Antischerotic Properties of Higher Fungi". Problems of Alimentation No. 1, 1989, pp 16–20).

However, these fungi are characterized by a low rate of growth (mycelium grows within 5–7 days while its fruit body, over 70 days) and possess a narrow range of physiological effect.

The fungi of Fusarium genus cultivated on the basis of modern biotechnology grow at a higher rate.

Known in the prior art is the strain of fungus *Fusarium sambucinum* Fuckel var. *ossicolum* (Berk. et Curt.) Bulai VSB-917—a producer of food or fodder protein (All-Union Collection of Industrial Microorganisms of the VNIIgenetika Institute, collection code VKPM F-169). This fungus, *Fusarium sambucinum* var *ossicolum* (Berk. et Curt.) Bulai VSB-917 was deposited in June 1981 with the Russian National Collection of Industrial Microorganism (VKPM) at 1 Poroznny proezd, Moscow, Russia, 113545 with the Accession number given by the International Depository Authority of VKPM F-169.

Formerly, this strain was named Polyporus sp. VSB-917 (Microbiol. Sciences, 1986, v. 3, No. 6, pp 168–171).

The strain *Fusarium sambucinum* Fuckel var. *ossicolum* (Berk. et Curt.) Bulai VSB-917 was produced at the active growth stage during continuous cultivation of mycelium of the *Fusarium sambucinum* PS-64 strain (All-Union Collection of Industrial Microorganisms of the VNIIgenetika Institute, collection code TsMPM-F-165).

The strain *Fusarium sambucinum* VSB-917, F-169 possesses the following cultural and physiological features: on wort agar it forms white felt colonies which turn pink with age, does not form fruit bodies; commissures not discovered. Characterized by two types of sporification: crescent-shaped conidia with 2–5 partitions, and chamydospores. Being cultivated in a liquid nutrient medium forms a multi-cellular filiform mycelium with ascomycetous partitions and Voronin bodies. In the active growth stage the hyphas are 2.5–3.5 microns thick, the mycelium cells are homogeneous, without lipide and other inclusions, the ends of hyphas (mycelium) are evenly rounded. On aging, the cells develop numerous inclusions of fat.

This strain is an aerobe, grows in a temperature interval of 22°–28° C. and a pH interval of 4.5–7.0, the optimum pH reaching 5.8. Does not dilute gelatine. Assimilates glucose, saccharose, lactose, maltose, galactose, raffinose, as well as starch, ethanol, glycerine, acetic acid, mannit, xylitol.

Attitude towards the source of nitrogen: assimilates ammonium salts, nitrates, urea, peptone.

Under the conditions of submerged cultivation the strain grows well on milk whey (4–6% lactose) with ADM (absolutely dry matter) yield of 20–25 g per one liter of nutrient medium.

The output of the drain-add process is 1.4–1.6 kg/cu m/h.

The mycelium of the strain produced by submerged cultivation was grown on the nutrient medium containing, wt. %: molasses, 4; ammonium nitrate, 0.3; acidic potassium phosphate, 0.2; tap water: at pH=6.0–6.2 of the medium before sterilization, a temperature of 26°–28° C. and a cultivation time of 16 h the mycelium was subjected to autolysis and the resulting autolysate in the amount of 0.25–1.0% was introduced into the nutrient medium for growing *Torulopsis candida* yeast (Inventor's Certificate USSR No. 1034401 of 18.03.82 C12 No. 1/16), which increased the content of protein in the mass of yeast and raised its concentration in the cultural medium from 31.1–32 g up to 34–44 g/l of absolutely dry matter.

The new application of the strain *Fusarium sambucinum* VSB-917 consists in using it as a producer of physiologically-active substances for prophylactic and curative applications.

DISCLOSURE OF THE INVENTION

The main object of the invention resides in using the stain *Fusarium sambucinum* VSB-917 as a base for developing a medicinal preparation featuring a wide range of physiological effects on the organism and having no contraindications for its administration.

The preparation based on the above-described strain has a wide range of curative and prophylactic effects because it contains a number of various physiologically-active substances, such as essential amino acids, immunomodulating polysaccharides, essential fatty acids, biological amines, ubiquinones, vitamins and microelements in natural relations. The preparation normalizes the disturbed metabolic processes in the organism which often lead to cardiovascular diseases, obesity, diabetes, immunodeficient troubles, avitaminoses. The preparation causes no allergic reactions, combines well with traditional therapeutic medicines, intensifying their effect on the organism and reducing unfavorable side effects, particularly when radiotherapy is administered to oncological patients.

We have studied the chemical composition of the preparation and probable pathogenicity, acute and chronic toxicity, teratogenicity in five generations of animals cancerogenicity and cocarcinogenicity. Investigations were conducted in compliance with the stipulations of the World Health Organization referring to examinations of substances of microbial origin. On the basis of this series of experiments the Public Health Authorities approved the application of the preparation under the commercial name "MILAIF" preparation.

| | |
|---|---|
| total protein | from 60 to 63 |
| true protein | from 42 to 46 |
| carbohydrates | from 10 to 13 |
| lipides | from 4 to 8 |
| nucleic acids | from 3 to 6 |
| mineral substances | from 6 to 8 |
| vitamins | from 2.6 to 3.1 |
| water | the balance. |

The protein components of "MILAIF" preparation include all essential amino acids (% of total protein): lysine, 9.2; isoleucine, 3.4; leucine, 4.5; phenyl–alanine+tyrosine, 4.5; cystine+methyonine, 2.3; threonine, 3.7; tryptophan, 0.8; valine, 3.6 which account for 35–45% of the sum of amino acids. With respect to this parameter the "MILAIF" preparation resembles muscle proteins, also containing 45% of essential amino acids. It is known that the protein substances and their derivatives play an important role in metabolic processes of digestion, respiration, discharges and motion. And the so-called "essential" amino acids must enter the human organism as an integral substance since they are not synthesized therein.

The carbohydrate part of "MILAIF" preparation amounting to 10–13% in terms of dry matter is represented by 1-3-β-D glycanes which display immonumodulating activity. (Kashkin M. A., Elinov N. G. "Immunomodulating Activity of Polysaccharides from Fungi", J. "Mycology and Phytopathology", vol. 19, Issue 4, 1985, pp 1–3).

The monomeric composition of these glycanes is represented by glucose, galactose, mannose and fructose in the relations of 1.0:1.38:1.79:0.5, respectively.

The lipid fraction of "MILAIF" preparation amounting to 4–8% in terms of dry matter contains physiologically-active substances of various types of compounds: phospholipides, sterols, glycerides, fatty acids. The data on their quantitative content are summarized in Table 1.

The physiologically-active phospholipides (phosphatidilserine, phosphatidilethanolamine and posphatidil choline) take part in various metabolic processes and in energy metabolism.

Phospholipides are the basic components in the structure of the cell membrane and cell organelles. Their functional role is based on control of permeability of cell membranes. They maintain the functioning of the cell mechanism, i.e. ion exchange, respiration, biological oxidation, they influence the activity of enzymes in mitochondria. The lack of phospholipides leads to disorders of fat metabolism and, eventually, to fat degeneration of the liver.

The fat-acid fraction of "MILAIF" preparation contains physiologically-active fatty acids belonging to the category of essential ones. Over 50% of the sum of fatty acids falls to linolic acid which is the predecessor of prostaglandins which regulate the hormonal activity of animals and man.

Owing to their known pharmacological properties, the phospholipides and nonsaturated fatty acids regenerate the damaged mitochondria, activate the disturbed enzyme systems, intensify the detoxicating function of the liver similarly to the known preparation Essentiale (M. D. Mashkovsky, "Medicinal Agents", "Meditsina" Publishers, Moscow, 1984, vol. 2, p. 46).

A high physiological activity is manifested by 22,23-dihydroergosterol, one of the vitamins of group D ($D_4$). Its activity is similar to that of cholecalcipherol (vitamin $D_3$), favoring a correct phosphocalcium exchange, particularly in growing organisms, and timely deposition of substances into growing bones. (M. D. Mashkovsky "Medicinal Agents", "Meditsina" Publishers, Moscow, 1984, p. 34).

TABLE 1

Contents of Physiologically-Active Components in Lipide Fraction of "MILAIF" preparation (mg/100 g of preparation)

| Physiologically-active substances | Quantity from | Quantity to |
|---|---|---|
| Phosphatidilserine | 0.12 | 0.28 |
| Phosphatidilethanolamine | 0.23 | 0.53 |
| Phosphatidilcholine | 0.79 | 0.85 |
| 22,23-dihydroergosterol | 4.0 | 5.0 |
| Monoglycerides | 46 | 92 |
| Triglycerides | 1136 | 2272 |
| Oleic acid $C_{18:1}$ | 0.8 | 1.6 |
| Linolic acid $C_{18:2}$ | 2.8 | 5.6 |
| Linolic acid $C_{48:3}$ | 0.03 | 0.09 |
| Ubiquinone $Q_9$ | 0.034 | 0.075 |
| Ubiquinone $Q_{10}$ | 0.054 | 0.125 |

Ubiquinone $Q_9$ (ubinone) is a metabolite of the organism of animals while ubiquinone $Q_{10}$, metabolite of man.

A comparative examination of ubinone and ubiquinone $Q_{10}$ with vitamin E (active antioxidant) has demonstrated that the antioxidating and anticytolytic activities of ubinone and ubiquinone $Q_{10}$ are 5 times that of vitamin E. Ubinone and ubiquinone $Q_{10}$ are 5 times more active than vitamin E and 1.5 times more active than lipoic acid, they normalize the detoxicating and excretory functions of the liver damaged by carbon tetrachloride.

Ubinone and ubiquinone $Q_{10}$ are general-purpose irreplaceable components in the functioning of biological membranes and metabolism of the cell as a whole, including hepatocytes in the organisms of animals and man. Their high hepatoprotective activity is a consequence of inhibiting of molecular membrane pathogenetic mechanisms associated with the intensified peroxide oxidation of lipids.

The known experimental data give ground to a conclusion that ubinone and ubiquinone $Q_{10}$ feature an antioxidating activity in the liver tissue suffering from toxic damage. Ubinone and ubiquinone $Q_{10}$ forestall cytolysis and necrosis of hepatocytes and normalize the excretory and detoxicating functions of the liver that have been affected by toxic hepatitis (L. V. Vinogradov, E. A. Obolnikova et al "Ubiquinones—Perspective Hepatoprotectors of Metabolic Type". The 1st Russian National Congress "Man and Medicaments", April 1992, Moscow, thesis 408).

Analyzing the composition of the lipide component of the "MILAIF" preparation preparation one can get convinced in its high physiological activity in the organism. The mineral composition of "MILAIF" preparation appears in Table 2, below.

TABLE 2

Mineral Composition of "MILAIF" preparation

| Element, concentration | Air-dry preparation |
|---|---|
| Moisture content, % | 5.95 |
| Ash, % | 10.87 |
| Sodium, mg/g | 1.74 |
| Potassium, mg/g | 17.37 |
| Calcium, mg/g | 44.0 |
| Magnesium, mg/g | 2.92 |
| Phosphorus, mg/g | 15.0 |

TABLE 2-continued

| Mineral Composition of "MILAIF" preparation | |
|---|---|
| Element, concentration | Air-dry preparation |
| Iron, μkg/g | 64.0 |
| Zinc, μkg/g | 18.0 |
| Copper, μkg/g | 10.0 |
| Manganese, μkg/g | 39.0 |
| Strontium, μkg/g | 4.76 |
| Cobalt, μkg/g | 2.0 |
| Nickel, μkg/g | 4.0 |
| Chromium, μkg/g | 3.0 |
| Lithium, μkg/g | under 0.004 |
| Rubidium, μkg/g | 3.16 |
| Molybdenum, μkg/g | 0.1 |
| Aluminum, μkg/g | 7.1 |
| Lead, μkg/g | 0.2 |
| Cadmium, μkg/g | 0.2 |
| Arsenic, μkg/g | 0.1 |
| Mercury, μkg/g | under 0.01 |

It follows from the data of Table 2 that "MILAIF" preparation contains a sizable amount of physiologically-active elements.

Calcium in the organism takes part in the building of bone tissue, activation of blood coagulating enzymes, reduces excitability of some nervous system sections, weakens the effect of toxins, improves resistance to infections, excites bioelectrical potentials on the surface of cell membranes.

Potassium normalizes intercellular pressure and activates many enzymes.

Phosphorus and its compounds function as a constituent part of bone tissue and teeth and takes part in energy-generating processes.

Copper participates in transformation of iron into forms available for the synthesis of hemoglobin.

Manganese influences synthesis of glycogen and takes part in normalization of carbohydrate metabolism.

Iron is included into hemoglobin; lack of iron results in a serious disease—anemia.

Thus, a wide spectrum of chemical elements contained in "MILAIF" preparation and the today's notions about their role in the organism of man confirm the physiological activity of this preparation.

The water-soluble vitamins contained in "MILAIF" preparation are listed in Table 3.

"MILAIF" preparation contains mainly vitamins of group B whose total quantity amounts to 2.6–3.1%.

TABLE 3

Content of Vitamins in "MILAIF" preparation Preparation

| Vitamins, mg % | Quantity from | Quantity to |
|---|---|---|
| $B_1$ (thiamine) | 11 | 13 |
| $B_2$ (riboflavin) | 56 | 64 |
| $B_3$ (panthotenic acid) | 38 | 49 |
| $B_4$ (choline) | 2300 | 2800 |
| $B_6$ (pyridoxine) | 9 | 10 |
| Folic acid | 1 | 2 |
| PP (nicotinic acid) | 206 | 231 |
| Biotin | 2 | 3 |
| $B_{12}$ (cyanocobalamin) | 8 | 9 |

Today, the physiological effect of Group B vitamins is well investigated. It has been established that they play an important part in the processes of protein, fat and carbohydrate metabolism, raise the resistance of the organism to contagious diseases due to their immunostimulating effect, participate in the synthesis of prostaglandins, enzyme and coenzymes, and display a strong prophylactic effect. In "MILAIF" preparation these vitamins are contained in the form of a natural complex which is a substantial advantage over their synthetic analogs and artificially evolved compositions (e.g. methiovit, Vitamin $B_1$).

Medicobiological Investigations of "MILAIF" Preparation

The object of medicobiological investigations of "MILAIF" preparation involved obtaining the data that guarantee the safety of its administration for curative and prophylactic purposes.

The investigations conducted on three kinds of animals (rats, hens, swine) have demonstrated that peroral administration of "MILAIF" preparation has brought about the following results:

- no negative effect under the conditions of acute (30 days), subchronic (60 days) and chronic (a year) experiment when 10, 25, 50 and 100% of the protein of vivarium fodder was replaced by "MILAIF" preparation;
- no carcinogenic effect nor modifying influence upon the development of spontaneous and induced tumors;
- no dominant lethal mutations in the sexual cells of animals;
- no teratogenic and embryotrophic effect in five generations of animals;
- no allergic effects;
- no effect on the weight of the heart, liver, kidneys, and spleen;
- no effect on morphological parameters of animal blood which remain within the limits of physiological norms.

A study of the "MILAIF" preparation preparation has revealed a higher activity of succinatedehydrogenase and a larger content of glycogen in the liver of rats whose protein demand was fully covered by the "MILAIF" preparation preparation. The content of fat was also observed to diminish in the liver of rats whose protein was derived only from "MILAIF" preparation.

Similar results were registered with swine fed in accordance with the established physiological norms.

The studies have been conducted on three groups of animals.

The first group has received conventional food wherein the protein component (30%) consisted of meat-and-bone meal.

The second group, same as the first one, received conventional fodder but the protein component (30%) was the protein of "MILAIF" preparation.

The results of these experiments are given below in Table 4.

TABLE 4

Parameters of Lipide Metabolism in Blood Serum or Swine Treated with "MILAIF" preparation

| Parameter, mg/l | Group I (meat-and-bone meal) | Group II "MILAIF" preparation |
|---|---|---|
| Cholesterin | 1525 ± 53 | 1302 ± 109 |
| Phospholipides | 1390 ± 95.2 | 1305 ± 70.1 |
| Triglycerides | 1238 ± 84 | 940 ± 112 |
| Total lipides | 4440 ± 134 | 3770 ± 135 |
| β-lipoproteides | 1200 ± 28 | 925 ± 70 |

These data are an evidence that "MILAIF" preparation exerts a favorable effect on lipide metabolism by decreasing substantially the content of cholesterin and triglycerides.

Clinical Studies of the Therapeutic Effect of "MILAIF" Preparation in Cases of Alimentary Obesity (Disturbed Lipide Metabolism)

It is commonly known that alimentary obesity inevitably brings about the development of pathology in various systems of the organism.

In this connection, "MILAIF" preparation was given to three groups of patients:

1. Patients suffering from obesity in combination with metabolic diseases (hypercholesterolemia, arterial hypertension, diabetes mellitus with disturbed tolerance to glucose)—45 persons.
2. Individuals suffering from obesity in combination with pathology of biliferous system (chrone cholecystitis, cholelithiasis, dyskinesia of biliferous tracts)—18 persons.
3. Cases of obesity in combination with pathology of gastroenteric tract (peptic ulcer, erosive gastritis and bulbitis, duodenitis)—12 persons.

1. Investigation of the Effect of "MILAIF" Preparation on Dynamics of Clinico-Biochemical Parameters in Patients Suffering from Obesity in Combination with Diseases of Metabolic Profile (TC), high-density lipoproteins (HDLP), triglycerides (TG), coefficient of atherogenicity (CA) have revealed a natural shift of these parameters (Table 5). Particular interest was caused by an analysis of the parameters that point to a risk of development of ischemic heart disease (IHD) since the overwhelming number of patients (33 persons) in the analyzed group were under 40 years of age.

The significance of the parameter HDLP/TC both for the entire group of patients and separately for men and women consisted in that they were in the zone of a high risk of development of this pathology: 17.6–18.7% against the normal 20–25%. The coefficient of atherogenicity reliably exceeded the normal values (4.5±0.4 against the normal 3.0).

In 50% of the observed patients we have noticed two risk factors leading to the development of IHD (hypercholesterolemia ad hypertension). After a course of treatment, we have observed a pronounced reduction of lipide parameters both in all patients and individually in the groups of men and women.

TABLE 5

Some Clinico-Biochemical Parameters of patients Suffering from Obesity in Combination with Diseases of Metabolic Profile

| | Loss of body | AP | | TC | | HDLP | |
|---|---|---|---|---|---|---|---|
| | weight (kg) | before | after | before | after | before | after |
| Group I (20 men) | 11.9 ± 1.1 | 140/95 | 120/80 | 7.8 ± 0.7 | 5.9 ± 0.4 | 1.47 ± 0.12 | 1.38 ± 0.09 |
| Group II (25 women) | 9.2 ± 2.1 | 157/100 | 129/90 | 8.04 ± 0.5 | 6.16 ± 0.3 | 1.4 ± 0.1 | 1.2 ± 0.09 |
| Entire group (45 persons) | 10.5 ± 1.6 | 148/97.5 | 124.5/85 | 7.92 ± 0.2 | 6.03 ± 0.1 | 1.43 ± 0.11 | 1.29 ± 0.07 |
| Control (15 persons) | 10.0 ± 1.2 | 149/96 | 126/87 | 7.37 ± 0.2 | 6.04 ± 0.1 | 1.75 ± 0.09 | 1.45 ± 0.08 |

| | Loss of body | HDLP/TC | | CA | | TG | |
|---|---|---|---|---|---|---|---|
| | weight (kg) | before | after | before | after | before | after |
| Group I (20 men) | 11.9 ± 1.1 | 18.7 ± 1.9 | 25.3 ± 2.8 | 4.3 ± 0.5 | 2.8 ± 0.3 | 1.7 ± 0.01 | 1.52 ± 0.02 |
| Group II (25 women) | 9.2 ± 2.1 | 17.6 ± 2.3 | 23.1 ± 2.6 | 4.7 ± 0.3 | 3.6 ± 0.24 | 1.6 ± 0.02 | 1.48 ± 0.01 |
| Entire group (45 persons) | 10.5 ± 1.6 | 17.8 ± 2.6 | 24.2 ± 2.7 | 4.5 ± 0.4 | 3.2 ± 0.25 | 1.65 ± 0.01 | 1.5 ± 0.01 |
| Control (15 persons) | 10.0 ± 1.2 | 23 ± 3.1 | 24 ± 1.8 | 3.2 ± 0.2 | 3.16 ± 0.3 | 1.61 ± 0.02 | 1.61 ± 0.01 |

Note:
AP - arterial pressure
TC - total cholesterine
HDLP - high density lipoproteides
HDLP/TC, % - relation of HDLP to total cholesterine
CA - coefficient of atherogenicity
TG - triglycerides The observed group of 45 patients suffered from obesity in combination with hypercholesterolemia (group I—20 men, Group II—25 women).

Investigations of such traditional parameters of lipid metabolism as content in blood serum of total cholesterine Particularly pronounced changes were registered in men: statistically significant reduction of cholesterine level, coefficient of atherogenicity, triglycerides and a higher value of HDLP/TC.

A comparison of the obtained results with the control data has revealed a more conspicuous effect in the patients treated with "MILAIF" preparation. The effect of traditional therapy was less pronounced.

A primary examination of 15 patients has demonstrated higher content of sugar in blood. After a careful examination (glycemic curve with a load of 75 g glucose, glycemic indices) diabetes mellitus, type II was diagnosed in 5 patients, and disturbed tolerance to glucose, in 10 patients. A statistically-significant depression of this factor in the group of patients receiving "MILAIF" preparation dropped from 7.54+0.9 mmol/l to 5.3+0.48 mmol/l as compared with control: 6.76+0.7 mmol/l to 6.32+0.6 mmol/l.

Tolerance of the preparation in all the patients was good. In 75% of observed patients a considerable reduction of the feeling of hunger and appetite was noticed. The loss of body weight was 11.9+1 kg in men and 9.2+2.1 kg in women.

2. Effect of "MILAIF" Preparation on the Dynamics of Clinico-biological Indices of Patients in Combination with Pathology of Hepatobiliary System 18 patients under observation had various kinds of pathology of the hepatobiliary system. Dyskinetic functional disorders such as hypermotor dyskinesia of bile-discharge tracts was discovered in 50% of cases. 50% of patients had a more pronounced organic pathology in the form of X-ray-confirmed cholelithiasis. At admission all patients complained of heaviness in the dextral hypochondrium, paroxysm-like pains due to nonobservance of proper diet and after a heavy physical strain. These patients suffered also from various dyspeptic troubles such as bitter taste, nausea after fatty food. The patients were given a traditional course of dietary therapy aimed at reducing the body weight combined with administration of bile-expelling agents.

"MILAIF" preparation was given during the therapeutic course for 21 days. Tolerance for the preparation was good in all the patients without exception. Appetite diminished in 75% of cases.

The dynamics of biochemical indices is shown in Table 6.

TABLE 6

Dynamics of Biochemical Indices in Patients Suffering from Obesity Combined with Pathology of Hepatobiliary System

| | Bilirubin | | TC | | HDLP | | TG | |
|---|---|---|---|---|---|---|---|---|
| | before | after | before | after | before | after | before | after |
| Observed patients | 27.8 ± 3.1 | 20 ± 4 | 8.5 ± 0.7 | 5.9 ± 0.4 | 1.5 ± 0.1 | 1.2 ± 0.2 | 1.7 ± 0.09 | 1.5 ± 0.2 |
| Control | 24.6 ± 4.2 | 20.2 ± 3.8 | 7.4 ± 0.9 | 6.4 ± 1.0 | 1.24 ± 0.1 | 1.26 ± 0.2 | 1.54 ± 0.1 | 1.54 ± 0.3 |

It can be deduced from the above data that the patients of this group of pathology suffered from abnormalities characteristic of the entire group of corpulent individuals as a whole. The growth of the values of serum bilirubin due to the bile-conjestion syndrome displayed a more significant tendency to reduction in the group of patients administered the test preparation. Other discovered results included reduced appetite and feeling of hunger, and a more pronounced depression of lipide values (TC, HDLP, TG) which leads to a conclusion about expediency of administering said preparation to this category of patients.

Thus, "MILAIF" preparation is capable of normalizing efficiently the values of cholesterine and triglycerides in blood serum of the patients suffering from cardiovascular diseases progressing against the background of disturbed lipoid metabolism, thereby diminishing the risk of the ischemic heart disease.

Investigations of Adaptogenic Effect of "MILAIF" Preparation

Investigations were conducted in 15 oncological patients 31 to 65 years old with various localization of tumors (carcinoma of uterine cervix, II and III stage, kidney cancer, III stage, lymphogranulomatosis). The control group consisted of 15 persons of the same age and localization of tumors. All patients were beam-cured with a single dose of 2–4 GR, a total of 40–60 GR. Leukopenia in all the "MILAIF" preparation receiving patients diminished in comparison with the control group (by 1600±370, P<0.05). Even in the cases with a low initial level of leukocytes ($1.7\times10^8$–$1.8\times10^8$) it was possible to raise it in two–five days to $3.0\times10^8$–$4.0\times10^8$ and, sometimes, even to $5.5\times10^8$. The number of leukocytes could be increased by the use of other biostimulators too, but "MILAIF" preparation demonstrated a higher stability of results.

The growth of the number of leukocytes was stable and often occurred in the course of continued irradiation which happens extremely seldom, particularly without blood transfusion. We were able to administer a complete course of beam-curing without unplanned breaks caused by leukopenia and blood transfusion.

The percentage of monocytes was high, though somewhat lower than that in the control group: the form of monocytes was exceeded only by 3–5% in 10 cases out of 15 while the remaining five and the control patients has a considerable monocytosis (18–26%).

All patients demonstrated diminished asthenia, improved appetite, sleep, and frame of mind.

Thus, the investigations testify to the fact that "MILAIF" preparation is an adaptogenic agent, protecting the organism against such a damaging factor as repeated irradiation.

The effect of "MILAIF" preparation was also studied in patients with spontaneous leukopenia (5 persons) and leukopenia induced by radiotherapy (11 persons). The leukocyte count was examined in the patients receiving "MILAIF" preparation for 15, 30 and 60 days (I stage) and during the repeated course after 12 months (II stage). The results are summarized in Table 7.

TABLE 7

Effect of "MILAIF" preparation on the Leukocyte Count during Prolonged Treatment of Leukopenia Patients

| Patients | No. of leukocytes before treatment | Duration of treatment, days 15 | 30 | 60 |
|---|---|---|---|---|
| | | Number of leukocytes after treatment | | |
| I STAGE | | | | |
| Total, 16 persons | 3195 ± 166 | 3936 ± 167 | 4807 ± 183 | 4750 ± 164 |
| Leukopenia caused by R-therapy, 11 persons | 3405 ± 168 | 4010 ± 172 | 4807 ± 173 | 4800 ± 165 |
| Spontaneous leukopenia, 5 persons | 2700 ± 151 | 3733 ± 154 | 3733 ± 196 | 4500 ± 161 |
| II STAGE | | | | |
| Treatment after 12 months Total, 16 persons | 3310 ± 158 | 4060 ± 161 | 4803 ± 171 | 4750 ± 158 |
| Leukopenia caused by R-therapy, 11 persons | 3350 ± 157 | 4000 ± 160 | 4600 ± 171 | 4800 ± 157 |
| Spontaneous leukopenia, 5 persons | 2800 ± 160 | 4310 ± 165 | 4807 ± 172 | 4500 ± 160 |

The children of the main group were given "MILAIF" preparation daily for 20–25 days.

The control group received standard treatment in hospital.

The children of both groups were carefully examined by a pediatrician, neuropathologist, otorhinolaryngologist, immunologist, microbiologist and other specialists.

Out of 56 children in the main group 38 proved to be sensitized to the tissues of the internal organs: 21 were diagnosed to suffer from chronic gastritis, 18 from chronic colitis with symptoms of dysbacteriosis, 32 from chronic choloecystitis and cholecystoangiocholitis.

Apart from the conventional investigations (total blood count, analyses of urine, feces, ECG) we have practised immunochemiluminiscent methods of examining blood and saliva for anti-organ and antibacterial antibodies on "Beta-2-analyzer" based on superlow glow of biological media and cells in the visible region of the spectrum, caused by lipide structures.

Changes in the autoimmunization values caused by administration of "MILAIF" preparation appear in Table 8.

TABLE 8

Dynamics of Autoimmunization Values after Administration of "MILAIF" preparation

| Kind of organ antigen | Intensity of formation of autoantibodies in arbitrary units of chemiluminescence Group I before | after | Intensity of formation of autoantibodies, arbitrary units of chemiluminescence Group II before | after | Control group test without antigen |
|---|---|---|---|---|---|
| Lung | 516.2 ± 34.1 | 476.0 ± 50.6 | 496.8 ± 26.1 | 401.2 ± 38 | 403.7 ± 30.8 |
| Spleen | 1270.5 ± 126.6 | 617.1 ± 99.0 | 1121 ± 39.7 | 991 ± 79.2 | 403.7 ± 30.8 |
| Kidney | 715.5 ± 40.0 | 512.8 ± 52.8 | 701.8 ± 52.3 | 501.8 ± 67.6 | 403.7 ± 30.8 |
| Liver | 1112.8 ± 36.5 | 618.8 ± 75.3 | 1122.9 ± 40.1 | 884.1 ± 36.2 | 403.7 ± 30.8 |
| Small intestine | 910.8 ± 78.4 | 572.8 ± 60.4 | 924.8 ± 76.8 | 612.1 ± 39.9 | 403.7 ± 30.8 |
| Stomach | 818.3 ± 35.4 | 490.0 ± 28.8 | 886.4 ± 32.8 | 727.3 ± 31.4 | 403.7 ± 30.8 |
| Pancreas | 701.4 ± 16.8 | 518 ± 50.5 | 694.1 ± 18.6 | 498.8 ± 39.7 | 403.7 ± 30.8 |
| Heart | 516.8 ± 40.2 | 503.8 ± 60.4 | 598.1 ± 40.2 | 412.1 ± 26.3 | 403.7 ± 30.8 |
| Large intestine | 854.6 ± 25.3 | 4554.7 ± 36.8 | 832.1 ± 33.1 | 511.1 ± 36.4 | 403.7 ± 30.8 |

The data of Table 7 show clearly the dynamics of the increased leukocyte count in the patients suffering from leukopenia of different etiologies.

Thus, the adaptogenic effect of "MILAIF" preparation is expressed by increased nonspecific resistance of the organism in cases of leukopenia of different etiologies.

Investigations of the Effect of "MILAIF" Preparation of Immune Processes

Investigations were conducted on children 3–5 years of age, residents of an ecologically-unfavorable area, with diagnosed overoxidation syndrome. The total number of examined children was 77: 56 in the main group (I) and 21 in the control group (II).

It can be concluded from Table 8 that the blood of the children in both main and control groups accumulates a large number of anti-organ antibodies and has a conspicuous autoimmunization to the tissues of spleen, liver, small and large intestines, and stomach. A comparison of treatment results of the main and control groups has proven that the reduction of autoimmunization efficiency in control children was less pronounced with respect to the digestive organs and unreliably diminished with relation to the tissues of spleen, lung, and heart.

Prescription of "MILAIF" preparation to the children of the main group for 20–25 days contributed to a reliable reduction of autoimmune antibodies circulating in blood with respect to the tissues of spleen, kidney, liver, stomach and intestines.

Hence, it is practicable that "MILAIF" preparation be prescribed in case of troubles with the digestive organs accompanied by an autoimmune process and weakening of the protective forces of the organism.

We have studied the effect of "MILAIF" preparation on the microflora in children of the same groups.

In 54.2% of the children we have noticed a derangement of one or more indices characteristic of cutaneous flora, in 38.2%, a high number of microorganisms per unit of skin surface, in 36.8%—mannit-decomposing bacteria and in 44.5%, hemolytic bacteria not typical of the healthy organism of a child.

Derangements in the microflora of intestines were characterized by a substantial reduction of inoculation rate of bifidobacteria, detection of collibacilli with a weakened fermenting activity, Escherichia in a lactose-negative form, and changes of normal relationships between various species of intestinal microflora due to appearance of a large number of coccus forms of staphylococcus and streptococcus).

In 6.4% of children the inoculations of feces showed the presence of Candida fungi in active state.

Therefore, this called for studying the possibility of developing the sensitization or bacterial infection of children with pathogenic autoflora and treating them with "MILAIF" preparation.

Sensitization to bacterial allergens was studied by the method of immunchemiluminescence.

The tests included determining the accumulation of bacterial antibodies in blood and saliva with relation to antigens of streptococcus, staphylococcus, colibacillus, Proteus, enterococcus, blue pus bacillus.

The study of bacterial infection and bacterial sensitization made it possible to register immunological reactions to bacterial antigens. The most frequent reaction in children of both the main and control groups was sensitization to colibacillus, staphylococcus and Proteus.

It turned out that changes in the microbial picture in children was habitually accompanied by intensified production of antibodies with relation to several bacteria simultaneously.

Table 9 summarizes the data obtained in studying the immune reactions with relation to bacterial antigens in the children of the main and control groups.

TABLE 9

Dynamics of Sensitization Level Relative to Bacterial Antigens

| Type of bacterial antigen | Hemiluminescence intensity, arbitrary units | | | | |
|---|---|---|---|---|---|
| | Test | Group I | | Group II | |
| | without antigen | before treatment | after treatment | before treatment | after treatment |
| *Hemolytic staphylococcus* | 165 ± 41 | 567 ± 75 | 263 ± 41 | 562 ± 76 | 389 ± 71 |
| *Hemolytic streptococcus* | 205 ± 77 | 382 ± 72 | 211 ± 34 | 401 ± 78 | 218 ± 78 |
| Colibacillus | 204 ± 46 | 701 ± 80 | 405 ± 48 | 688 ± 81 | 512 ± 73 |
| Proteus | 189 ± 56 | 590 ± 58 | 519 ± 76 | 548 ± 49 | 521 ± 38 |
| Blue pus bacillus | 178 ± 45 | 443 ± 48 | 297 ± 68 | 463 ± 44 | 366 ± 48 |
| Enterococcus | 211 ± 64 | 372 ± 52 | 228 ± 38 | 370 ± 56 | 254 ± 67 |

It follows from the Table that administration of "MILAIF" preparation to children of the main group contributed to a pronounced reduction of concentration of antibodies to hemolytic staphylococcus, streptococcus, colibacillus, enterococcus and blue pus bacillus.

Hence, it is expedient that "MILAIF" preparation be prescribed to children with symptoms of dysbacteriosis developed against the background of inhibited protective forces of the organism.

Thus, administration of "MILAIF" preparation to the patients suffering from such chronic diseases as cholecystoangiocholitis, gastritis, gastroduodenitis, colitis often with symptoms of dysbacteriosis developed against the background of overoxidation syndrome has reduced the conspicuousness of autoimmune reactions, mainly to the antigens of the gastroenteric tract and hyposensitization to several bacterial allergens simultaneously.

Practical Applicability

The strain of the fungus *Fusarium sambucinum* VSB-917 is utilized for commercial production of the "MILAIF" preparation preparation.

The claimed preparation will prove its worth in public health services and can be used as:

- an additional therapeutic agent in cases of disturbed metabolism of lipides, cholesterine and glucose (atherosclerosis, ischemic heart disease, liver troubles, obesity, diabetes of II type), particularly in gerontology;
- a prophylactic agent against somatic diseases and complications developing against the background of radio therapy in oncological patients;
- an auxiliary medicine for administration during general health-improving and deintoxicating therapy;
- a prophylactic preparation against somatic diseases of individuals living and working in ecologically unfavorable conditions and heavy radiation zones;
- a medicament for treatment of dysbacteriosis;
- a cure for avitaminoses;
- a means for correction of microelements.

Bearing in mind its autoimmune activity, the preparation can be sued in transplantation of organs and tissues.

Description of the Method for Production of the "MILAIF" Preparation Preparation The process for producing the preparation comprises the following steps:

- preparation and sterilization of a liquid nutrient medium;
- preparation of the inoculation mycelium of the fungus;
- growing mycelium in fermenting apparatuses;
- condensing, extracting, drying and packing the preparation.

The source of carbon required for the growth of mycelium can be sugar beet and cane molasses, raw sugar, saccharose, glucose, waste of alcohol and cognac industry (alcohol and cognac grains), milk whey, juices and roots and green mass. Sodium, potassium and phosphorus are produced from ammonium nitrate and acidic potassium phosphate.

The nutrient medium is sterilized in a continuous sterilizer at a temperature of 125°±2° C. for 3 min. The inoculation mycelium for the fermenting apparatus is grown first in vitro on a solid nutrient medium then in vibrating flasks in a liquid nutrient medium and, finally, in an inoculating apparatus under the following conditions:

temperature—25°±2° C.

pH—5.5–6.2 aeration—1 cu m/cu m/min.

The inoculum is considered ready when concentration of dry matter of mycelium in the cultural medium reaches 9–12 g/l. This medium in the amount of 5–10 wt. % serves as the inoculum which is transferred in aseptic conditions into the fermenting apparatus.

Mycelium is cultivated in the fermenting apparatus under the same conditions as in the inoculator and on the nutrient medium of the same composition. The process of cultivation may be either of the periodic drain-add type, or continuous.

The following technological step is condensing the cultural medium in vacuum filters. Then the product is dehydrated in infrared driers under mild temperature conditions (up to plus 50° C.) at which the biological activity of components is retained.

The drying time is 15–20 min.

Finally, the preparation is granulated, pelleted and packed.

The term of storage of the thus-produced preparation without loss of its activity is 24 months at room temperature (17°–25° C.).

Given below are Examples of composition of the claimed "MILAIF" preparation preparation.

EXAMPLE 1

The mycelium of fungus was grown by the drain-add cultivation method in a 200-l fermenting apparatus on the following nutrient medium, wt. %:

| | |
|---|---|
| beet molasses | 4 (2 in terms of reducing matter) |
| ammonium nitrate | 0.3 |
| acidic potassium phosphate | 0.2 |
| water | ad 100 |
| pH | 5.5–5.8. |

The inoculum was introduced in the amount of 5 vol. %, at a cultivation temperature of 24°±1° C., duration of one cultivation cycle, 14 h. The content of absolutely dry matter was 20 g per 1 l of medium. Process productivity—1.4 kg/cu m/h.

The resulting preparation had the following composition, wt. %:

| | |
|---|---|
| Total protein (N × 6.25) | 60 |
| Carbohydrates | 13 |
| Lipides | 8 |
| Nucleic acids | 3 |
| Mineral substances | 8 |
| Vitamins | 2.6 |
| Water | 5.4. |

EXAMPLE 2

Mycelium was grown by "drain-add" method in 30-l fermenting apparatuses on the nutrient medium of the following composition, wt. %:

| | |
|---|---|
| Raw sugar | 2 |
| Ammonium nitrate | 0.3 |
| Acidic potassium phosphate | 0.2 |
| Maize extract | 0.05 |
| Water | ad 100 |
| pH | 5.7–6.0. |

The inoculum was introduced in the amount of 8 wt. %, the cultivation temperature was 25°±1° C. Duration of cycle—13 h. Then 92% of the cultural medium was drained, a new cultrueal medium was added and cultivation was continued. The operation was repeated after 13 h. The concentration of absolutely dry matter was 20:1 g/l.

The process efficiency was 1.5 kg/cu m/h.

The resulting preparation had the following composition, wt. %:

| | |
|---|---|
| Total protein (N × 6.25) | 63 |
| Carbohydrates | 10 |
| Lipids | 4 |
| Nucleic acids | 6 |
| Mineral substances | 6 |
| Vitamins | 3.1 |
| Water | 7.9. |

EXAMPLE 3

Mycelium was grown as in Example 2 except that the inoculum was introduced in the amount of 10 vol. %. Cultivation temperature 26°±1° C., pH of medium, 6.0–6.2.

In this case the duration of cultivation was 12.5 h and accumulation of absolutely dry matter, 20.2 g/l.

Process efficiency, 1.6 kg/cu m/h.

The composition of the preparation was as follows, wt. %:

| | |
|---|---|
| Total protein (N × 6.25) | 61.5 |
| Carbohydrates | 11.5 |
| Lipids | 6 |
| Nucleic acids | 4.5 |
| Mineral substances | 7 |
| Vitamins | 2.8 |
| Water | 6.7. |

We claim:

1. A method of treating a disease selected from the group consisting of: obesity, radiation-induced leucopenia and increased autoimmune antibodies in the spleen, kidney, liver, large intestines or stomach caused by infection or bacterial antigens from Staphyloccus, Streptococcus, Colibacillus, Enteroccus or blue pus Bacillus, comprising administering to an animal in need of said treatment an effective amount of a cell culture of the fungus *Fusarium Sambucinum* var. *ossicolum* (Berk. et Curt.) Bulai VSB-917.

2. The method according to claim 1, wherein the cell culture has the following composition, by weight %:

| | |
|---|---|
| protein | 60–63 |
| carbohydrates | 10–13 |
| lipids | 4–6 |
| nucleic acids | 3–6 |
| minerals | 6–8 |
| vitamins | 2.6–3.1. |

3. The method of claim 1, wherein the animal is a human.

4. The method of claim 3, wherein the disease treated is obesity.

5. The method of claim 3, wherein the disease treated is radiation induced leucopenia.

6. The method of claim 4, wherein the disease treated is increased autoimmune antibodies in the spleen, kidney, liver, large intestines or stomach caused by infection or bacterial antigens from Staphyloccus, Streptococcus, Colibacillus, Enteroccus or blue pus Bacillus.

7. The method of claim 4, wherein the cell culture is in the form of tablets, granules or powder.

* * * * *

8. A method of reducing blood levels of compounds selected from the group consisting of glucose, triglycerides and cholesterol comprising administering an effective amount of a cell culture of the fungus *Fusarium Sambucinum* var. *ossicolum* (Berk. et Curt.) Bulai VSB-917 to an animal in need of such treatment.

9. The method of claim 8, wherein the animal is a human.

10. The method of claim 9, wherein the blood level of glucose is reduced.

11. The method of claim 9, wherein the blood level of triglycerides and cholesterol is reduced.

12. The method of claim 8, wherein the cell culture has the following composition by weight %:

| | |
|---|---|
| protein | 60–63 |
| carbohydrates | 10–13 |
| lipids | 4–6 |
| nucleic acids | 3–6 |
| minerals | 6–8 |
| vitamins | 2.6–3.1. |

13. The method of claim 8, wherein the cell culture is administered in the form of tablets, granules, or powder.

14. The method of claim 8, wherein the blood level of glucose is reduced.

15. The method of claim 9, wherein the cell culture is in the form of tablets, granules, or powder.

* * * * *

UNITED STATES PATENT AND TRADEMARK OFFICE

CERTIFICATE OF CORRECTION

PATENT NO. : 5,759,543

DATED : June 2, 1998

INVENTOR(S) : Galina R. MOROZOVA et al.

It is certified that error appears in the above-indentified patent and that said Letters Patent is hereby corrected as shown below:

On the cover page, item [73] *Assignee*, second line, change "Miakop." to --Maikop--;

in column 16, line 60, change "4" to --3--;

line 66, change "4" to --3--;

Signed and Sealed this

Twenty-ninth Day of February, 2000

Attest:

Q. TODD DICKINSON

*Attesting Officer*

*Commissioner of Patents and Trademarks*